US00PP09624P

United States Patent [19]

Goemans

[11] Patent Number: Plant 9,624

[45] Date of Patent: Aug. 13, 1996

[54] ALSTROEMERIA PLANT NAMED 'LITTLE ELEANOR'

[75] Inventor: Frank Goemans, Sussex, England

[73] Assignee: Wuelfinghoff Alstroemeria B.V., Rijswijk, Netherlands

[21] Appl. No.: 434,389

[22] Filed: May 3, 1995

[51] Int. Cl.[6] ..... A01H 5/00

[52] U.S. Cl. ..... Plt./37.1

[58] Field of Search ..... Plt./37.1

*Primary Examiner*—James R. Feyrer
*Attorney, Agent, or Firm*—Foley & Lardner

[57] ABSTRACT

A new and distinct cultivar of Alstroemeria plant named 'Little Eleanor', particular characterized by its dwarf habit permitting the plant to be grown and marketed as a pot plant.

1 Drawing Sheet

The present invention comprises a new and distinct cultivar of Alstroemeria plant referred to by the culivar named 'Little Eleanor'.

Little Eleanor' was originated by inventor Frank Goemans from a hybridization made in a controlled breeding program in Chichester, Sussex, England in 1991. The identity and origin of the female parent is unknown at this time. The male parent was a selection out of a population of plants of *Alstroemeria aurantiaca,* a wild species also known as *A. aurea.* The selection was unnamed and was not identified by breeding number.

'Little Eleanor' was discovered and selected as one flowering plant within the progeny of the stated parentage in June 1991 by Frank Goemans in Chichester, England. The new cultivar was recognized immediately by its dwarf habit.

The first act of asexual reproduction of 'Little Eleanor' was accomplished when vegetative cuttings were taken from the initial selection in August 1991 in a controlled environment in Chichester, England by Frank Goemans. Horticultural examination of selected units initiated in June 1993 has demonstrated that the combination of characteristics as herein disclosed for the 'Little Eleanor' are firmly fixed and retained through successive generations of asexual reproduction.

'Little Eleanor' has not been observed under all possible enviromental conditions. The phenotype may vary somewhat with variations in environment such as temperature, light intensity and day length, without, however, any variance in genotype. The following observations, measurements and comparisons describe plants grown in Spalding Lincs, England under greenhouse conditions which approximate those generally used in commercial practice.

The following traits have been repeatedly observed and are determined to be unique characteristics of 'Little Eleanor' which distinguish this Alstroemeria as a new and distinct cultivar:

1. To the best knowledge of the inventor, the new cultivar is the first genetic dwarf Alstroemeria cultivar. This is of significant commercial importance.

2. Due to its dwarf habit, the new cultivar can be marketed as a pot plant, thereby establishing a new market for Alstroemeria.

Because of its unique dwarf habit, there is no cultivar with which 'Little Eleanor' can be meaningfully compared.

The accompanying color photographic drawings show typical size, inflorescence and foliage characteristics of 'Little Eleanor', with colors being as nearly true as possible with illustrations of this type.

The photograph at the top of the sheet comprises a typical pot-grown plant of 'Little Eleanor'.

The photograph at the bottom of the sheet is a close up view showing more clearly the flowers and buds of the new cultivar. Colors are as accurate as possible with color presentations of this type. The photographs are of a three (3) month old plant.

In the following description color references are made to the Royal Horticultural Society Color Chart. The color values were determined during the afternoon in May 1993 under normal daylight conditions, at Wageningen, The Netherlands.

Classification:

*Botanical.*—Alstroemeria cv 'Little Eleanor'.
*Commercial.*—Alstroemeria.

PLANT

Form: Round, symmetrical pot plant.
Height: 10 inches, measured from top of pot and based on three (3) month old plant.
Growth: Compact, short and somewhat spreading habit.
Foliage:
*Quantity.*—average in number.
*Size of leaf.*—Length is short, width is medium.
*Shape of leaf.*—Narrow-ovate.
*Color.*—Upperside, dark green; underside light green.
Rhizomes:
*Color.*—White.
*Size.*—Normal.

INFLORESCENCE

A. Bud:
*Form.*—Normal.
*Diameter.*—0.5 inch.
*Length.*—Short.
*Calyx.*—Elliptic.
B. Flower:
*Size.*—Medium, approximately 3 inches in diameter.
Borne: Medium number of branches in umbel.
Blooming habit:
Shape: Broad, elliptic.
Color:
*Upper surface.*—12A–13A; white at top center and base of large petals; dark reddish-brown streaks on inner petals.
*Under surface.*—white.
*Peduncle.*—Length, 10 inches; Color, medium green.
*Lasting quality.*—6 weeks.

REPRODUCTIVE ORGANS

Stamens: 6 in number.
Anthers: Color, light brown.

Filaments: Color, yellow.

Pistils: 1 in number; Color light brown.

Stigma: Color, yellow-white.

I claim:

1. A new and distinct cultivar of Alstroemeria plant named 'Little Eleanor', as illustrated and described.

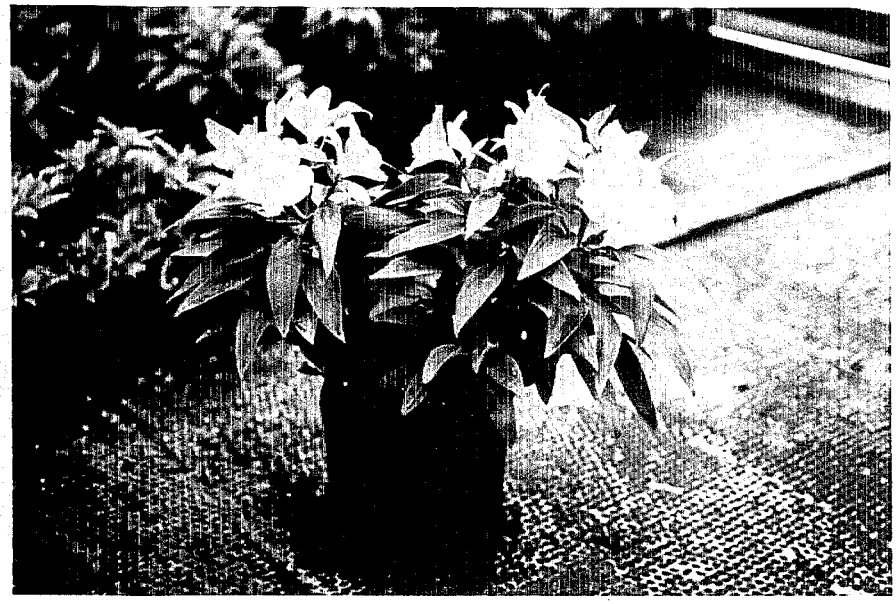
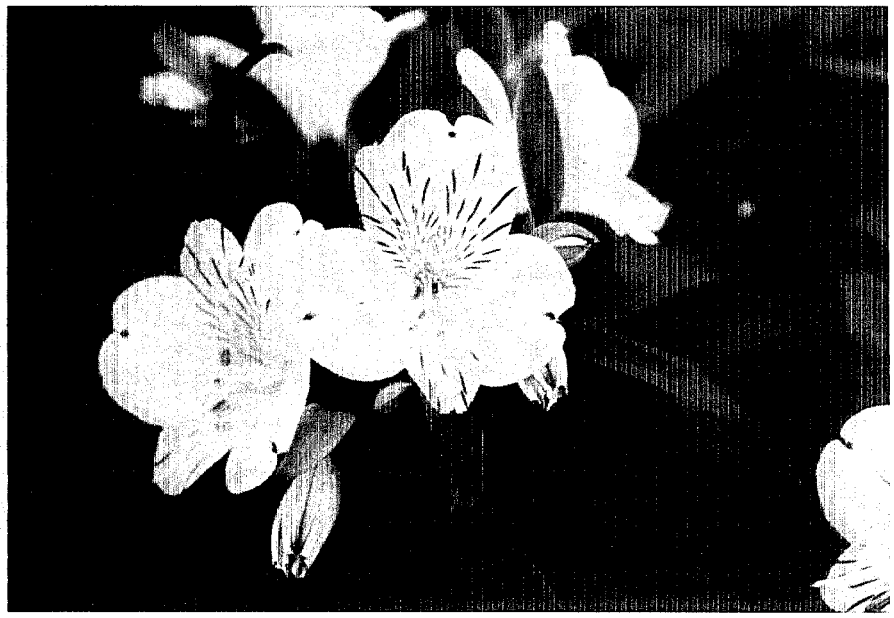

* * * * *